US009457042B2

(12) United States Patent
Westermarck et al.

(10) Patent No.: US 9,457,042 B2
(45) Date of Patent: Oct. 4, 2016

(54) PHARMACEUTICAL COMBINATION COMPRISING A CIP2A SILENCING AGENT FOR USE IN THE TREATMENT OF A HYPERPROLIFERATIVE DISORDER, PREFERABLY ONE WITH IMPAIRED P53 FUNCTION

(75) Inventors: Jukka Westermarck, Turku (FI); Anna Cvrljevic, Lemu (FI)

(73) Assignee: TURUN YLIOPISTO, Turku (FI)

( * ) Notice: Subject to any disclaimer, the term of this patent is extended or adjusted under 35 U.S.C. 154(b) by 0 days.

(21) Appl. No.: 14/343,015

(22) PCT Filed: Sep. 6, 2012

(86) PCT No.: PCT/FI2012/050862
§ 371 (c)(1),
(2), (4) Date: Mar. 5, 2014

(87) PCT Pub. No.: WO2013/034806
PCT Pub. Date: Mar. 14, 2013

(65) Prior Publication Data
US 2014/0199415 A1    Jul. 17, 2014

Related U.S. Application Data

(60) Provisional application No. 61/531,337, filed on Sep. 6, 2011.

(30) Foreign Application Priority Data

Sep. 6, 2011 (FI) .................................. 20115876

(51) Int. Cl.
| C07H 21/02 | (2006.01) |
| C07H 21/04 | (2006.01) |
| A61K 31/7088 | (2006.01) |
| A61K 31/436 | (2006.01) |
| A61K 31/337 | (2006.01) |
| A61K 31/404 | (2006.01) |
| A61K 31/4188 | (2006.01) |
| A61K 31/517 | (2006.01) |
| A61K 31/553 | (2006.01) |
| A61K 45/06 | (2006.01) |
| A61K 31/15 | (2006.01) |
| A61K 31/4545 | (2006.01) |
| A61K 31/5377 | (2006.01) |
| A61K 31/7068 | (2006.01) |
| A61K 31/713 | (2006.01) |
| A61K 33/24 | (2006.01) |
| A61K 38/00 | (2006.01) |
| A61K 31/00 | (2006.01) |
| A61K 31/09 | (2006.01) |
| A61K 31/165 | (2006.01) |
| A61K 31/166 | (2006.01) |
| A61K 31/245 | (2006.01) |

(Continued)

(52) U.S. Cl.
CPC .......... *A61K 31/7088* (2013.01); *A61K 31/00* (2013.01); *A61K 31/09* (2013.01); *A61K 31/15* (2013.01); *A61K 31/165* (2013.01); *A61K 31/166* (2013.01); *A61K 31/245* (2013.01); *A61K 31/282* (2013.01); *A61K 31/337* (2013.01); *A61K 31/404* (2013.01); *A61K 31/407* (2013.01); *A61K 31/4184* (2013.01); *A61K 31/4188* (2013.01); *A61K 31/436* (2013.01); *A61K 31/444* (2013.01); *A61K 31/4406* (2013.01); *A61K 31/4545* (2013.01); *A61K 31/4725* (2013.01); *A61K 31/497* (2013.01); *A61K 31/498* (2013.01); *A61K 31/506* (2013.01); *A61K 31/513* (2013.01); *A61K 31/517* (2013.01); *A61K 31/519* (2013.01); *A61K 31/5375* (2013.01); *A61K 31/5377* (2013.01); *A61K 31/55* (2013.01); *A61K 31/551* (2013.01); *A61K 31/553* (2013.01); *A61K 31/7068* (2013.01); *A61K 31/713* (2013.01); *A61K 31/7105* (2013.01); *A61K 33/24* (2013.01); *A61K 38/00* (2013.01); *A61K 45/06* (2013.01)

(58) Field of Classification Search
CPC ............................. C12N 15/113; A61K 48/00
See application file for complete search history.

(56) References Cited

U.S. PATENT DOCUMENTS

| 2003/0143732 A1 | 7/2003 | Fosnaugh et al. |
| 2003/0148507 A1 | 8/2003 | Fosnaugh et al. |

(Continued)

FOREIGN PATENT DOCUMENTS

| CN | 101352444 A | 1/2009 |
| WO | WO 2007/104835 A1 | 9/2007 |

(Continued)

OTHER PUBLICATIONS

Scherer et al. (Nat. Biotechnol., 2003, 21(12).*

(Continued)

*Primary Examiner* — Amy Bowman
(74) *Attorney, Agent, or Firm* — Birch, Stewart, Kolasch & Birch, LLP

(57) ABSTRACT

The invention is based on a finding that silencing CIP2A (KI-AA1524) gene sensitizes cancer cells for apoptosis-inducing activity of certain small molecule chemotherapeutic agents. Thus, the invention is directed to a respective combination therapy, sensitization method and pharmaceutical compositions. The invention further relates to a method of selecting cancer therapy for a subject on the basis of CIP2A and p53 expression and/or protein activity in a sample obtained from said subject.

3 Claims, 6 Drawing Sheets

(51) Int. Cl.

| | |
|---|---|
| A61K 31/282 | (2006.01) |
| A61K 31/407 | (2006.01) |
| A61K 31/4184 | (2006.01) |
| A61K 31/4406 | (2006.01) |
| A61K 31/444 | (2006.01) |
| A61K 31/4725 | (2006.01) |
| A61K 31/497 | (2006.01) |
| A61K 31/498 | (2006.01) |
| A61K 31/506 | (2006.01) |
| A61K 31/513 | (2006.01) |
| A61K 31/519 | (2006.01) |
| A61K 31/5375 | (2006.01) |
| A61K 31/55 | (2006.01) |
| A61K 31/551 | (2006.01) |
| A61K 31/7105 | (2006.01) |

(56) References Cited

U.S. PATENT DOCUMENTS

| | | |
|---|---|---|
| 2003/0175950 A1 | 9/2003 | McSwiggen |
| 2003/0190635 A1 | 10/2003 | McSwiggen |
| 2004/0019001 A1 | 1/2004 | McSwiggen |
| 2005/0008617 A1 | 1/2005 | Chen et al. |
| 2005/0043266 A1 | 2/2005 | Jayasena et al. |
| 2005/0255487 A1 | 11/2005 | Khvorova et al. |
| 2009/0239244 A1 | 9/2009 | Shi et al. |

FOREIGN PATENT DOCUMENTS

| | | |
|---|---|---|
| WO | WO 2007/147613 A2 | 12/2007 |
| WO | WO 2008/094321 A2 | 8/2008 |
| WO | WO 2009/100173 A2 | 8/2009 |

OTHER PUBLICATIONS

Vogel et al. (The Oncologist, 1999, 4, 47-33).*

Charl et al., "The p53 tumor suppressor network in cancer and the therapeutic modulation of cell death," Apoptosis (2009), vol. 14, pp. 336-347.

Chen et al., "Bortezomib Sensitizes HCC Cells to CS-1008, an Antihuman Death Receptor 5 Antibody, through the inhibition of CIP2A," Mol. Cancer Ther. (May 2011), vol. 10, No. 5, pp. 892-901.

Choi et al., "Increase in CIP2A expression is associated with doxorubicin resistance," FEBS Letters (2011), vol. 585, pp. 755-760.

Cui et al., "OptiRNAi, an RNAi design tool," Computer Methods and Programs in Biomedicine (2004), vol. 75, pp. 67-73.

Denlinger et al., "Proteasome Inhibition Sensitizes Non-Small-Cell Lung Cancer to Gemcitabine-Induced Apoptosis," Ann. Thorac. Surg. (2004), vol. 78, pp. 1207-1214.

International Search Report issued Nov. 12, 2012, in PCT International Application No. PCT/FI2012/050662.

Junttila et al., "CPI2A Inhibits PP2A in Human Malignancies," Cell (Jul. 13, 2007), vol. 130, pp. 51-62.

Khanna et al., "MYC-Dependent Regulation and Prognostic Role of CIP2A in Gastric Cancer," J. Natl. Cancer Inst. (2009), vol. 101, pp. 793-805.

Kim et al., "Synthetic dsRNA Dicer substrates enhance RNAi potency and efficacy," Nature Biotechnology (Feb. 2005), vol. 23, No. 2, pp. 222-226.

Li et al., "Ribozyme technology for cancer gene target identification and validation." Adv. Cancer Res. (2007), vol. 96, pp. 103-143.

Lin et al, "Combination of Proteasome and HDAC Inhibitors for Uterine Cervical Cancer Treatment," Clin. Cancer Res. (2009), vol. 15, pp. 570-577.

Ma et al., "Overexpression and Small Molecule-Triggered Downregulation of CIP2A in Lung Cancer," PLoS ONE (May 2011), vol. 6, No. 5, e20159, pp. 1-10.

Search Report issued May 22, 2012, in Finnish Patent Appication No. 20115876.

Silva et al. "Second-generation shRNA libraries covering the mouse and human genomes." Nature Genetics (Nov. 2005), vol. 11, pp. 1281-1288.

Vassilev et al., "In Vivo Activation of the p53 Pathway by Small-Molecule Antagonists of MDM2," Science (2004), vol. 303, pp. 844-848.

Westermarck, J. and W. C. Hahn, "Multiple pathways regulated by the tumor suppressor PP2A in transformation," Trends in Molecular Medicine, vol. 14, No. 4, pp. 152-160.

Zhao et al., "Functional genetics and experimental models of human cancer," Trends in Molecular Medicine (Jul. 2004), vol. 10, No. 7, pp. 344-350.

Zubkowicz et al., "Cytotoxic activity of rapamycin, the mTOR kinase inhibitor, used alone or in combination with bortezomib, proteasome inhibitor, on multiple myeloma cells in vitro," Acta Haematologica Polonica (2006), vol. 37, No. 3, pp. 373-386.

\* cited by examiner

SEQUENCE LISTING

```
<160> NUMBER OF SEQ ID NOS: 25

<210> SEQ ID NO 1
<211> LENGTH: 23
<212> TYPE: DNA
<213> ORGANISM: Artificial Sequence
<220> FEATURE:
<223> OTHER INFORMATION: siRNA molecule

<400> SEQUENCE: 1
aacataagtg cttcactgat ctt                                            23

<210> SEQ ID NO 2
<211> LENGTH: 23
```

```
<212> TYPE: DNA
<213> ORGANISM: Artificial Sequence
<220> FEATURE:
<223> OTHER INFORMATION: siRNA molecule

<400> SEQUENCE: 2
aactgtggtt gtgtttgcac ttt                                            23

<210> SEQ ID NO 3
<211> LENGTH: 21
<212> TYPE: DNA
<213> ORGANISM: Artificial Sequence
<220> FEATURE:
<223> OTHER INFORMATION: siRNA molecule

<400> SEQUENCE: 3
gguugcagau ucugaauuat t                                              21

<210> SEQ ID NO 4
<211> LENGTH: 21
<212> TYPE: DNA
<213> ORGANISM: Artificial Sequence
<220> FEATURE:
<223> OTHER INFORMATION: siRNA molecule

<400> SEQUENCE: 4
aaugccuugu cuaggauuat t                                              21

<210> SEQ ID NO 5
<211> LENGTH: 21
<212> TYPE: DNA
<213> ORGANISM: Artificial Sequence
<220> FEATURE:
<223> OTHER INFORMATION: siRNA molecule

<400> SEQUENCE: 5
accauugaua uccuuagaat t                                              21

<210> SEQ ID NO 6
<211> LENGTH: 29
<212> TYPE: DNA
<213> ORGANISM: Artificial Sequence
<220> FEATURE:
<223> OTHER INFORMATION: shRNA sense sequence

<400> SEQUENCE: 6
gatagcaatg atccacagtt taagtggtg                                      29

<210> SEQ ID NO 7
<211> LENGTH: 29
<212> TYPE: DNA
<213> ORGANISM: Artificial Sequence
<220> FEATURE:
<223> OTHER INFORMATION: shRNA sense sequence

<400> SEQUENCE: 7
ctttgtcggc acaatctttc tgttcaaac                                      29

<210> SEQ ID NO 8
<211> LENGTH: 29
<212> TYPE: DNA
<213> ORGANISM: Artificial Sequence
<220> FEATURE:
<223> OTHER INFORMATION: shRNA sense sequence

<400> SEQUENCE: 8
```

```
gtacttggag aaagtatagc agcaaacaa                                       29

<210> SEQ ID NO 9
<211> LENGTH: 29
<212> TYPE: DNA
<213> ORGANISM: Artificial Sequence
<220> FEATURE:
<223> OTHER INFORMATION: shRNA sense sequence

<400> SEQUENCE: 9
cagttgacct actgatggat ctccttaag                                       29

<210> SEQ ID NO 10
<211> LENGTH: 22
<212> TYPE: DNA
<213> ORGANISM: Artificial Sequence
<220> FEATURE:
<223> OTHER INFORMATION: shRNA sense sequence

<400> SEQUENCE: 10
cgcagattct gaattatgca aa                                              22

<210> SEQ ID NO 11
<211> LENGTH: 22
<212> TYPE: DNA
<213> ORGANISM: Artificial Sequence
<220> FEATURE:
<223> OTHER INFORMATION: shRNA sense sequence

<400> SEQUENCE: 11
agcacataaa gacattgagt aa                                              22

<210> SEQ ID NO 12
<211> LENGTH: 22
<212> TYPE: DNA
<213> ORGANISM: Artificial Sequence
<220> FEATURE:
<223> OTHER INFORMATION: shRNA sense sequence

<400> SEQUENCE: 12
attcctgata gatcacattc aa                                              22

<210> SEQ ID NO 13
<211> LENGTH: 22
<212> TYPE: DNA
<213> ORGANISM: Artificial Sequence
<220> FEATURE:
<223> OTHER INFORMATION: shRNA sense sequence

<400> SEQUENCE: 13
cacgtcagat aatagagaac aa                                              22

<210> SEQ ID NO 14
<211> LENGTH: 22
<212> TYPE: DNA
<213> ORGANISM: Artificial Sequence
<220> FEATURE:
<223> OTHER INFORMATION: shRNA sense sequence

<400> SEQUENCE: 14
catggatgta tatgaaatga aa                                              22

<210> SEQ ID NO 15
<211> LENGTH: 22
<212> TYPE: DNA
<213> ORGANISM: Artificial Sequence
```

```
<220> FEATURE:
<223> OTHER INFORMATION: shRNA sense sequence

<400> SEQUENCE: 15
ccggcacaat ctttctgttc aa                                              22

<210> SEQ ID NO 16
<211> LENGTH: 22
<212> TYPE: DNA
<213> ORGANISM: Artificial Sequence
<220> FEATURE:
<223> OTHER INFORMATION: shRNA sense sequence

<400> SEQUENCE: 16
agcacataaa gacattgagt aa                                              22

<210> SEQ ID NO 17
<211> LENGTH: 22
<212> TYPE: DNA
<213> ORGANISM: Artificial Sequence
<220> FEATURE:
<223> OTHER INFORMATION: shRNA sense sequence

<400> SEQUENCE: 17
cgcaaacttg ctgctgatgt aa                                              22

<210> SEQ ID NO 18
<211> LENGTH: 22
<212> TYPE: DNA
<213> ORGANISM: Artificial Sequence
<220> FEATURE:
<223> OTHER INFORMATION: shRNA sense sequence

<400> SEQUENCE: 18
ccggcacaat ctttctgttc aa                                              22

<210> SEQ ID NO 19
<211> LENGTH: 21
<212> TYPE: DNA
<213> ORGANISM: Artificial Sequence
<220> FEATURE:
<223> OTHER INFORMATION: shRNA sense sequence

<400> SEQUENCE: 19
cgcagcaagt tgaatcagaa a                                               21

<210> SEQ ID NO 20
<211> LENGTH: 21
<212> TYPE: DNA
<213> ORGANISM: Artificial Sequence
<220> FEATURE:
<223> OTHER INFORMATION: shRNA sense sequence

<400> SEQUENCE: 20
ccacagttta agtggtggaa a                                               21

<210> SEQ ID NO 21
<211> LENGTH: 21
<212> TYPE: DNA
<213> ORGANISM: Artificial Sequence
<220> FEATURE:
<223> OTHER INFORMATION: shRNA sense sequence

<400> SEQUENCE: 21
gctagtatgt tgagagaagt t                                               21
```

```
<210> SEQ ID NO 22
<211> LENGTH: 21
<212> TYPE: DNA
<213> ORGANISM: Artificial Sequence
<220> FEATURE:
<223> OTHER INFORMATION: shRNA sense sequence

<400> SEQUENCE: 22
gctagtagac agagaacata a                                              21

<210> SEQ ID NO 23
<211> LENGTH: 21
<212> TYPE: DNA
<213> ORGANISM: Artificial Sequence
<220> FEATURE:
<223> OTHER INFORMATION: shRNA sense sequence

<400> SEQUENCE: 23
gacagaaact cacacgacta t                                              21

<210> SEQ ID NO 24
<211> LENGTH: 21
<212> TYPE: DNA
<213> ORGANISM: Artificial Sequence
<220> FEATURE:
<223> OTHER INFORMATION: shRNA sense sequence

<400> SEQUENCE: 24
ccacagttta agtggtggaa a                                              21

<210> SEQ ID NO 25
<211> LENGTH: 21
<212> TYPE: DNA
<213> ORGANISM: Artificial Sequence
<220> FEATURE:
<223> OTHER INFORMATION: shRNA sense sequence

<400> SEQUENCE: 25
cggcacaatc tttctgttca a                                              21
```

PHARMACEUTICAL COMBINATION COMPRISING A CIP2A SILENCING AGENT FOR USE IN THE TREATMENT OF A HYPERPROLIFERATIVE DISORDER, PREFERABLY ONE WITH IMPAIRED P53 FUNCTION

CROSS REFERENCE TO RELATED APPLICATIONS

This non-provisional application is a National Stage entry under U.S.C. §371 of International Application No. PCT/FI2012/050862 filed on Sep. 6, 2012, which claims the benefit of U.S. Provisional Application No. 61/531,337 filed on Sep. 6, 2011 and to Finnish Patent Application No. 20115876 filed in Finland on Sep. 6, 2011. The entire contents of all of the above applications are hereby incorporated by reference.

FIELD OF THE INVENTION

This invention relates to the field of combination cancer therapeutics.

BACKGROUND OF THE INVENTION

Cancer is a devastating disease afflicting all communities worldwide. It has been estimated that 1 out of 2 men and 1 out 3 women will develop some form cancer within their lifetime.

Interestingly, it has been recently established that, regardless of the phenotypic variability between different cancer types, perturbation of limited number of genetic elements is sufficient to induce cellular transformation in many different human cell types (reviewed in (Zhao et al., 2004)). Experimentally, it was demonstrated that activation of Ras and telomerase (TERT), along with inactivation of the tumor suppressor proteins p53 and Retinoblastoma protein (Rb) can immortalize a variety of human cell types, which can subsequently transform to a tumorigenic state in response to inhibition of protein phosphatase 2A (PP2A). Therefore, these common genetic elements could be considered as master regulators of cancer development (Zhao et al., 2004).

PP2A is a widely conserved protein serine/threonine phosphatase (PSP) that functions as a trimeric protein complex consisting of a catalytic subunit (PP2Ac or C), a scaffold subunit (PR65 or A), and one of the alternative regulatory B subunits. As described above, recent experimental evidence has firmly established that inhibition of PP2A activity is a prerequisite for human cell transformation (reviewed in (Westermarck and Hahn, 2008)). Nevertheless, very little is known about mechanisms regulating PP2A complex composition and/or activity in vivo. Identification of PP2A inhibiting mechanisms might provide opportunities for development of novel class of cancer therapeutics reactivating PP2A tumor suppressor activity. This idea would be similar to cancer therapy approaches aiming at re-activation of tumor suppressor activity of p53 by small-molecules such as Nutlin-3 (Vassilev et al., 2004).

In 2007 a novel PP2A inhibitor protein designated Cancerous inhibitor of PP2A (CIP2A) was identified (Junttila et al., 2007). CIP2A interacts with PP2A and with one of the most important oncogenic transcription factors MYC. Moreover, siRNA-mediated depletion of CIP2A markedly increased PP2A activity in the MYC-PP2A complex and resulted in MYC serine 62 dephosphorylation and MYC protein degradation. It has also been demonstrated that CIP2A is required for the malignant cellular growth and for in vivo tumor formation (Junttila et al., 2007; Khanna et al., 2009; Westermarck and Hahn, 2008). Moreover, recent work has demonstrated overexpression of CIP2A in several common human malignancies and validated its role as a clinically relevant human oncoprotein (Khanna et al., 2009; Westermarck and Hahn, 2008). Thus, these results demonstrate that CIP2A is a novel human oncoprotein that inhibits PP2A in human malignancies.

Cell killing and/or apoptosis are the preferable endpoints for cancer therapy regimens. On the other hand, either intrinsic or acquired resistance is the major problem related to currently used chemotherapies. Thus, although at least some of the mechanisms underlying malignancy have been revealed, there exists a need in the art for the development of medicaments for hyperproliferative diseases and especially cancer. Activation of tumor suppressor protein p53 mediates apoptosis induction of cells in response to variety of the chemotherapeutics in clinical use. (Chari et al., 2009). However, as p53 function is impaired in approximately 50-70% of human cancers this is an important cause of chemotherapy resistance. (Chari et al., 2009). p53 is inactivated in cancer in most cases either by genetic mutations or by overexpression of negative regulators of p53 such as MDM2 or viral proteins such as human papillomavirus (HPV) 16 E6 protein. Thus, approaches that sensitizes those cancer cells that harbour functionally impaired p53 to chemotherapy are clearly needed in order to overcome the drug resistance (Chari et al., 2009).

BRIEF DESCRIPTION OF THE INVENTION

In one aspect, the invention provides a combination of at least one type of a CIP2A silencing agent and a chemotherapeutic agent selected from the group consisting of small molecule tyrosine kinase inhibitors, PARP inhibitors, CHK1 inhibitors, glucosinolates, alkylating agents, plant alkaloids, PI3K/mTOR inhibitors, histone deacetylases, DNA-PK inhibitors, STAT inhibitors, antimetabolites, and surviving inhibitors for use as a medicament in the treatment of hyperproliferative disorders comprising cells with impaired p53 function. Suitable agents of each category agents are set forth in claim 1.

In a further aspect, the invention provides pharmaceutical composition comprising a combination of CIP2A silencing agent and a chemotherapeutic agent according to the present invention and at least one pharmaceutically acceptable carrier.

In a still further aspect, the present invention provides a method of sensitizing hyperproliferative cells to a chemotherapeutic agent by silencing CIP2A gene in a human or animal subject in need of such sensitization.

In an even still further aspect, the invention provides a method of treating a hyperproliferative disease in a human or animal subject in need of such treatment by administering at least one type of CIP2A silencing agent and a compound selected from the group consisting of small molecule tyrosine kinase inhibitors, PARP inhibitors, CHK1 inhibitors, glucosinolates, alkylating agents, plant alkaloids, PI3K/mTOR inhibitors, histone deacetylases, DNA-PK inhibitors, STAT inhibitors, antimetabolites, and surviving inhibitors concomitantly, simultaneously, or subsequently to said subject. Suitable compounds of each category are set forth in claim 8.

Furthermore, one aspect of the present invention provides a method of selecting a cancer therapy for a subject in need of such therapy, wherein the method comprises evaluating CIP2A and p53 expression and/or protein activity in a sample obtained from said subject, and selecting monotherapy by at least one chemotherapeutic agent for subjects whose sample is negative for CIP2A expression and/or activity and impaired for p53 activity, and selecting a combination therapy according to the present embodiments for subjects whose sample is positive for CIP2A expression and impaired for p53 activity.

In some embodiments of the above aspects, said CIP2A silencing agent is selected from the group consisting of an sRNA molecule, DsiRNA molecule, artificial miRNA precursor, shRNA molecule, antisense oligonucleotide, ribozyme, and agent preventing CIP2A function towards PP2Ac. In further embodiments, the CIP2A silencing agent comprises as a nucleic acid sequence selected from the group consisting of SEQ ID NO:s 1 to 25, and sequences having at least 80% sequence identity to said SEQ ID NO:s 1 to 25 and retaining their CIP2A silencing activity.

In some embodiments, of the above aspects, the hyperproliferative disorder to be treated is selected from a group consisting of psoriasis, myocardial hypertrophy, benign tumors, solid cancers and haematological cancers. Non-examples of said solid cancers include squamous cell carcinomas of the head and neck, colon cancer, gastric cancer, breast cancer, ovarian cancer, prostate cancer, cervical cancer, esophageal cancer, lung cancer, liver cancer, brain cancer, glioma, astrocytoma, and glioblastoma, whereas non-limiting examples of haematological cancers include acute and chronic T-cell and B-cell leukemias and lymphomas.

Other specific embodiments, objects, details, and advantages of the invention are set forth in the dependent claims, following drawings, detailed description and examples.

BRIEF DESCRIPTION OF THE DRAWINGS

In the following the invention will be described in greater detail by means of preferred embodiments with reference to the attached drawings, in which.

DETAILED DESCRIPTION OF THE INVENTION

Figure 1:
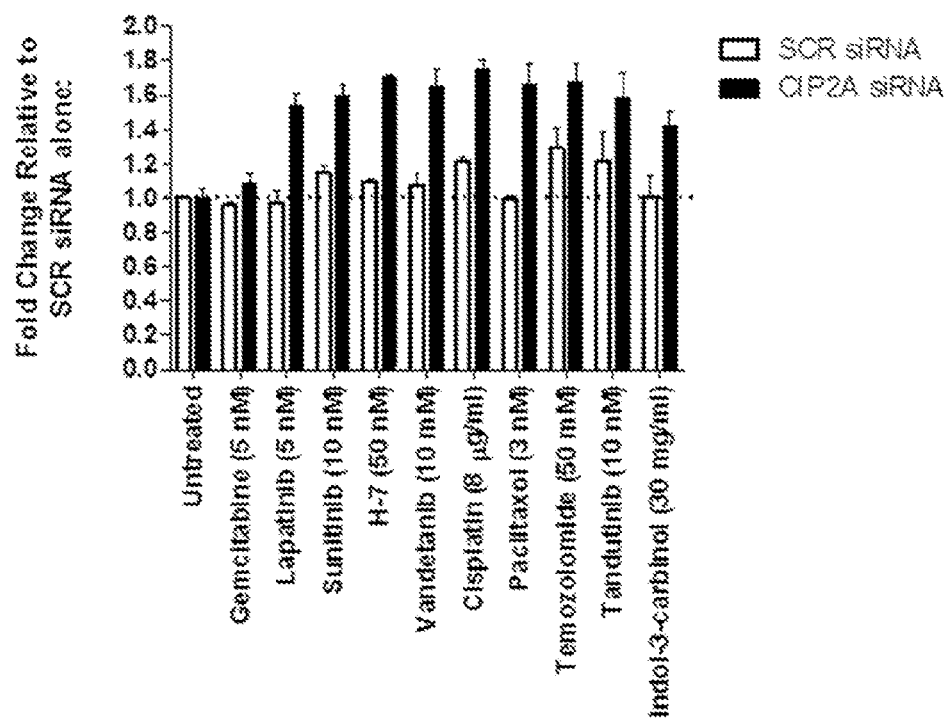
FIG. 1 shows the level of apoptosis (i.e. Caspase 3/7 activity), induced in the human derived glioma cell line, T98G, following the inhibition of CIP2A with siRNA in combination with standard chemotherapeutic agents when compared to SCR siRNA transfected cells alone.

The present invention is based on a surprising finding that silencing CIP2A gene sensitizes cancer cells compromised for p53 tumor suppressor protein function for apoptosis-inducing activity of certain small molecule chemotherapeutic agents. Concomitant silencing of CIP2A gene and administration of said chemotherapeutic agent results in either additive or synergistic increase in the level of apoptosis and/or other type of cell death in cells in which p53 function has become inhibited. On the other hand, the invention shows that CIP2A negative lymphoma cells expressing mutated p53 are more sensitive to monotherapy with said chemotherapeutic agents. Thus, in one aspect, the invention provides a combination therapy of CIP2A depletion and said chemotherapeutic agents, while in another aspect the invention provides a method for stratification of cancer patients for chemotherapy by detection of CIP2A and p53 status of patient samples.

The present patient stratification method comprises determining the CIP2A and p53 status of a cancer tissue sample obtained from said patient. Patients with CIP2A negative and p53 inactivated cancer cells should be selected for monotherapy treatment with chemotherapeutic agents, whereas patients with CIP2A positive and p53 inactivated cancer cells should be treated with the present combination therapy, i.e. CIP2A inhibition together with administration of certain chemotherapeutic agents.

The level of CIP2A in a cancer tissue sample or a bodily fluid may be determined by various means. For instance, the level of the CIP2A protein in a tissue or body fluid may be quantified by i) determining the CIP2A mRNA expression from said tissue or body fluid by RT-PCR, or by a hybridizing technique, or ii) subjecting the tissue or body fluid expected to contain the protein CIP2A to an antibody recognizing said CIP2A, and detecting and/or quantifying said antibody, or subjecting said tissue or body fluid to analysis by proteomics techniques. Suitable hybridizing techniques include, for example DNA hybridization and northern blot. The detection or quantification of the antibody can be performed according to standard immunoassay protocols, such as label-linked immunosorbent assays, western blot and immunohistochemical methods.

Impaired function of p53 in a cancer tissue or a bodily fluid sample may be determined by standard methods known to those skilled in the art. The method of choice depends, at least partly, on the mechanism underlying the impaired p53 function. For instance, detection of p53 inactivating mutations may be performed by hybridisation techniques or by DNA or RNA sequencing or by RT-PCR analysis of the RNA or DNA, as well known to a person skilled in the art. Overexpression of negative regulators of p53 such as MDM2 or viral proteins such as human papillomavirus (HPV) 16 E6 protein, may be determined the same way as the level of CIP2A.

The patient stratification method can be carried out by determining the status of CIP2A and p53 alone or with the same in combination with other proteins or genes.

CIP2A gene silencing may be obtained by any suitable method known in the art including, but not limited to, RNA interference (RNAi). The most common approach for RNAi-based gene silencing is the use of small interfering RNA (siRNA).

The principle of siRNA is extensively presented in literature. As examples can be mentioned the US patent publications 2003/0143732, 2003/0148507, 2003/0175950, 2003/0190635, 2004/0019001, 2005/0008617 and 2005/0043266. A siRNA duplex molecule comprises an antisense region and a sense strand wherein said antisense strand comprises sequence complementary to a target region in an mRNA sequence encoding a certain protein, and the sense strand comprises sequence complementary to the said antisense strand. Thus, the siRNA duplex molecule is assembled from two nucleis acid fragments wherein one fragment comprises the antisense strand and the second fragment comprises the sense strand of said siRNA molecule. In other words, siRNAs are small double-stranded RNAs (dsRNAs). The sense strand and antisense strand can be covalently connected via a linker molecule, which can be a polynucleotide linker or a non-nucleotide linker. The length of the antisense and sense strands may vary and is typically about 19 to 21 nucleotides each. In some cases, the siRNA may comprise 22, 23 or 24 nucleotides.

Another approach for RNAi-based CIP2A silencing is to use longer, typically 25-35 nt, Dicer substrate siRNAs (DsiRNAs), which in some cases have been reported to be more potent than corresponding conventional 21-mer siRNAs (Kim et al., 2005). DsiRNAs are processed in vivo into active siRNAs by Dicer.

In a cell, an active siRNA antisense strand is formed and it recognizes a target region of the target mRNA. This in turn leads to cleaving of the target RNA by the RISC endonuclease complex (RISC=RNA-induced silencing complex) and also in the synthesis of additional RNA by RNA dependent RNA polymerase (RdRP), which can activate Dicer and result in additional siRNA duplex molecules, thereby amplifying the response.

As used herein, the term "dsRNA" refers to both siRNAs and DsiRNAs.

Typically, but not necessarily, the antisense strand and the sense strand of dsRNA both comprise a 3'-terminal overhang of a few, typically 1 to 3 nucleotides. The 3' overhang may include one or more modified nucleotides, such as a 2'-O-methyl ribonucleotide. The 5'-terminal of the antisense is typically a phosphate group (P). The dsRNA duplexes having terminal phosphate groups (P) are easier to administrate into the cell than a single stranded antisense. In some cases, the 5'-terminal of the sense strand or of both antisense and sense strands may comprise a P group.

Normal, unmodified RNA has low stability under physiological conditions because of its degradation by ribonuclease enzymes present in the living cell. If the oligonucleotide shall be administered exogenously, it is highly desirable to modify the molecule according to known methods so as to enhance its stability against chemical and enzymatic degradation.

Modifications of nucleotides to be administered exogenously in vivo are extensively described in the art (e.g. in US 2005/0255487, incorporated herein by reference). Principally, any part of the nucleotide, i.e the ribose sugar, the base and/or internucleotidic phosphodiester strands can be modified. For example, removal of the 2'-OH group from the ribose unit to give 2'-deoxyribosenucleotides results in improved stability. Prior disclosed are also other modifications at this group: the replacement of the ribose 2'-OH group with alkyl, alkenyl, allyl, alkoxyalkyl, halo, amino, azido or sulfhydryl groups. Also other modifications at the ribose unit can be performed: locked nucleic acids (LNA) containing methylene linkages between the 2'- and 4'-positions of the ribose can be employed to create higher intrinsic stability.

Furthermore, the internucleotidic phosphodiester linkage can, for example, be modified so that one or more oxygen is replaced by sulfur, amino, alkyl or alkoxy groups. Also the base in the nucleotides can be modified.

Preferably, the oligonucleotide comprises modifications of one or more 2'-hydroxyl groups at ribose sugars, and/or modifications in one or more internucleotidic phosphodiester linkages, and/or one or more locked nucleic acid (LNA) modification between the 2'- and 4'-position of the ribose sugars.

Particularly preferable modifications are, for example, replacement of one or more of the 2'-OH groups by 2'-deoxy, 2'-O-methyl, 2'-halo, e.g. fluoro or 2'-methoxyethyl. Especially preferred are oligonucleotides where some of the internucleotide phoshodiester linkages also are modified, e.g. replaced by phosphorothioate linkages.

In some embodiments, dsRNAs may contain one or more synthetic or natural nucleotide analogs including, but not limited to, phosphorothioates, phosphoramidates, methyl phosphonates, chiral-methyl phosphonates, and peptide-nucleic acids (PNAs) as long as dsRNAs retain their CIP2A silencing ability.

It should be stressed that the modifications mentioned above are only non-limiting examples.

One of the challenges related to RNAi is the identification of a potent dsRNA for the corresponding mRNA. It should be noted that genes with incomplete complementarity are inadvertently downregulated by the dsRNA, leading to problems in data interpretation and potential toxicity. This however can be partly addressed by carefully designing appropriate dsRNAs with design algorithms. These computer programs sieve out given target sequence with a set of rules to find sequence stretches with low GC content, a lack of internal repeats, an NU rich 5-end and high local free binding energy which are features that enhance the silencing effect of dsRNA.

In order to identify agents useful in the present invention, several different CIP2A siRNAs were designed by using commercial and non-commercial algorithms. To this end, full length cDNA sequence of CIP2A (KIAA1524) was loaded to siRNA algorithm programs (Eurofins MWG Operon's Online Design Tool) and stand-alone program developed by Cui et al. (Cui et al., 2004). Further, algorithm generated siRNA sequences were then screened trough genome wide DNA sequence alignment (BLAST) to eliminate siRNAs which are not free from off-targeting. In other words, all those siRNAs which had even short sequence regions matching with other genes than target gene (CIP2A) were considered invaluable for further use.

Obtained siRNAs were then transfected to different cell lines and their capacity to degrade mRNA and further deplete translation of CIP2A was studied at protein level by measuring the amount of CIP2A protein after siRNA treatment with CIP2A specific antibodies (Table 1).

TABLE 1

CIP2A specific siRNAs

| SEQ ID NO | siRNA sense sequence (5' to 3') | % CIP2A inhibition (protein level) |
|---|---|---|
| 1 | 5'-AACATAAGTGCTTCACTGATCTT-3' | Moderate |
| 2 | 5'-AACTGTGGTTGTGTTTGCACTTT-3' | High |
| 3 | 5'-GGUUGCAGAUUCUGAAUUATT-3' | Moderate |
| 4 | 5-AAUGCCUUGUCUAGGAUUATT-3' | Low |
| 5 | 5'-ACCAUUGAUAUCCUUAGAATT-3' | High |

Suitable dsRNAs include those having a greater than 80% sequence identity, e.g., 80%, 81%, 82%, 83%, 84%, 85%, 86%, 87%, 88%, 89%, 90%, 91%, 92%, 93%, 94%, 95%, 96%, 97%, 98%, 99% or even 100% sequence identity with SEQ ID NO:s 1 to 5, as long as they have similar or enhanced binding properties and CIP2A silencing activity as the reference dsRNAs.

Still further CIP2A specific dsRNAs suitable for use in various embodiments of the present invention can be designed and synthetized according to methods known in the art. Any such isolated dsRNA must be sufficiently complementary to CIP2A cDNA sequence in order to silence CIP2A gene.

Artificial microRNA (miRNA) precursors are another class of small RNAs suitable for mediating RNAi. Typically, artificial miRNA precursors are about 21-25 nucleotides in length, and they may have 1 to 3, typically 2, overhanging 3' nucleotides. CIP2A silencing artificial miRNA precursors may be designed and synthetized by methods known in the art.

Short-hairpin RNAs (shRNAs) are still another way of silencing CIP2A. ShRNAs consist of i) a short nucleotide sequence, typically ranging from 19 to 29 nucleotides, derived from the target gene; ii) a loop, typically ranging between 4 to 23 nucleotides; and iii) a short nucleotide sequence reversely complementary to the initial target sequence, typically ranging from 19 to 29 nucleotides. ShRNA expression cassette may also contain sequences that increase the RNA interference activity. Non-limiting examples of such sequences are microRNA sequence of mir-30 as shown by Silva et al (Silva et al., 2005).

CIP2A silencing shRNAs may be designed and synthetized by means and methods known to a skilled person. Non-limiting examples of suitable sense sequences (i.e. nucleotide sequences i) above) for use in CIP2A shRNAs are listed in Table 2. ShRNAs depicted in SEQ ID NO:6 to SEQ ID NO:9 are available e.g. from Origene, while shRNAs depicted in SEQ ID NO:10 to SEQ ID NO:25 are available e.g. from Open Biosystems.

TABLE 2

Sense sequences of CIP2A specific shRNAs

| SEQ ID NO | siRNA sense sequence (5' to 3') |
|---|---|
| 6 | 5'-GATAGCAATGATCCACAGTTTAAGTGGTG-3' |
| 7 | 5'-CTTTGTCGGCACAATCTTTCTGTTCAAAC-3' |
| 8 | 5'-GTACTTGGAGAAAGTATAGCAGCAAACAA-3' |
| 9 | 5-CAGTTGACCTACTGATGGATCTCCTTAAG-3' |
| 10 | 5'-CGCAGATTCTGAATTATGCAAA-3' |
| 11 | 5'-AGCACATAAAGACATTGAGTAA-3' |
| 12 | 5'-ATTCCTGATAGATCACATTCAA-3' |
| 13 | 5'-CACGTCAGATAATAGAGAACAA-3' |
| 14 | 5'-CATGGATGTATATGAAATGAAA-3' |
| 15 | 5'-CCGGCACAATCTTTCTGTTCAA-3' |
| 16 | 5'-AGCACATAAAGACATTGAGTAA-3' |
| 17 | 5'-CGCAAACTTGCTGCTGATGTAA-3' |
| 18 | 5'-CCGGCACAATCTTTCTGTTCAA-3' |
| 19 | 5'-CGCAGCAAGTTGAATCAGAAA-3' |
| 20 | 5'-CCACAGTTTAAGTGGTGGAAA-3' |
| 21 | 5'-GCTAGTATGTTGAGAGAAGTT-3' |
| 22 | 5'-GCTAGTAGACAGAGAACATAA-3' |
| 23 | 5'-GACAGAAACTCACACGACTAT-3' |
| 24 | 5'-CCACAGTTTAAGTGGTGGAAA-3' |
| 25 | 5'-CGGCACAATCTTTCTGTTCAA -3' |

Suitable shRNAs include those having a greater than 80% sequence identity, e.g., 80%, 81%, 82%, 83%, 84%, 85%, 86%, 87%, 88%, 89%, 90%, 91%, 92%, 93%, 94%, 95%, 96%, 97%, 98%, 99% or even 100% sequence identity with SEQ ID NO:s 6 to 25, as long as they have similar or enhanced binding properties and CIP2A silencing activity as the reference shRNAs.

CIP2A silencing may also be obtained by antisense therapy, where relatively short (typically 13-25 nucleotides) synthetic single-stranded DNA or RNA oligonucleotides inactivate CIP2A gene by binding to a corresponding mRNA. Antisense oligonucleotides may be unmodified or chemically modified. In some embodiments, the hydrogen at the 2'-position of ribose is replaced by an O-alkyl group, such as methyl. In further embodiments, antisense oligonucleotides may contain one or more synthetic or natural nucleotide analogs including, but not limited to PNAs.

Furthermore, CIP2A silencing may obtained by ribozymes cleaving the CIP2A mRNA. The ribozyme technology is described, for example, by Li et al. (Li et al., 2007).

As used herein, the term "CIP2A silencing" refers to complete or partial reduction of CIP2A gene expression. In some embodiments, CIP2A gene expression is reduced by at least 50%, or at least 80%, 81%, 82%, 83%, 84%, 85%, 86%, 87%, 88%, 89%, 90%, 91%, 92%, 93%, 94%, 95%, 96%, 97%, 98%, 99%, or 100% when CIP2A-specific dsRNA, artificial miRNA precursor, shRNA, antisense oligonucleotide, ribozyme, or any combination thereof is introduced into a human or animal subject.

In some embodiments, CIP2A silencing may be obtained by blocking or inhibiting the interaction between CIP2A and PP2A, especially the csubunit of PP2A, thus preventing CIP2A function towards PP2Ac at least 50%, or at least 80%, 81%, 82%, 83%, 84%, 85%, 86%, 87%, 88%, 89%, 90%, 91%, 92%, 93%, 94%, 95%, 96%, 97%, 98%, 99%, or 100%. Such blocking or inhibiting agents include, but are not limited to, recombinantly or chemically produced modified or unmodified peptides and partial peptides, as well as non-peptide molecules, such as small molecule chemical compounds. Methods for identifying such agents have been disclosed e.g. in WO 2009/100173 and US 2009/239244.

Chemical compounds suitable for use in various embodiments of the present invention include those listed in Table 3 and any stereoisomers, salts, solvates, or prodrugs thereof.

TABLE 3

Chemical Compounds

| Class of Drug | Chemotherapy Drug | Synonyms | Molecular Formula |
|---|---|---|---|
| Small Molecute Tyrosine Kinase Inhibitors | Lapatinb | INN. Tycerb ® | $C_{29}H_{28}CFN_4O_4S$ |
| | Tandutinb | | $C_{31}H_{42}N_6O_4$ |
| | Vandatanb | INN. ZD6474, Zactima | $C_{22}H_{24}BrFN_4O_2$ |
| | Dasatinb | BMS 354825 Sprycal | $C_{22}H_{26}ClN_2O_2S$ |
| | PKC-412 | Midostauin Benzoylstaurosporine | $C_{35}H_{30}N_4O_4$ |
| | H-7 | | $C_{14}H_{17}N_3O_2S \cdot 2HCl$ |
| | Sunlinib | SU11248 | $C_{22}H_{27}FN_4O_2$ |
| PARP Inhibitors | ABT-888 | Velparib | $C_{13}H_{18}N_4O \cdot 2HCl$ |
| | AG-014699 | | $C_{18}H_{16}FN_2O \cdot H_3PO_4$ |
| | IND-71677 | BSI-201, triparb, NSC-746045 | $C_2H_3IN_2O_3$ |
| | Olaparib | | $C_{25}H_{23}FN_4O_3$ |
| | PARP inhibitor III (DPQ) | 3,4-Dihydro-5[4-(1-piperindinyl)butoxy]-1(2H)-isoquinoine | $C_{18}H_{35}N_2O_2$ |
| CHK1 Inhibitors | UCN-01 | 7-Hydroxystaurosporine | $C_{28}H_{28}N_4O_4$ |
| | AZD7762 | 5-(3-Fluorophenyl)-3-ureidothiophene-N-[(S)-piperidin-3-yl]-2-carboxamide | $C_{17}H_{20}CFN_4O_2S$ |
| | PF-477736 | PF-0044736 | $C_{22}H_{25}N_7O_2$ |
| | SB 218078 | | $C_{24}H_{15}N_3O_3$ |
| | G86 976 | PD 406976, Go 6 976 | $C_{24}H_{18}N_4O$ |
| Glucosinolates | Indol-3-carbinol | I3C | $C_9H_9NO$ |
| Alkylating Agents | Cisplatin | CDDP, Plainol ® | $Cl_2H_8N_2Pl$ |
| Plant Alkaloids | Temozolomide | TMZ, Temodal, Temodar ® | $C_5H_8N_8O_2$ |
| PI3K (p110_/_)/mTOR Inhibitors | Pacliaxel | Taxol ®, Onxes ™ | $C_{47}H_{51}NO_{14}$ |
| | Vinorebine | Vinorebine tartrate, Nevebine ® | $C_{45}H_{34}N_4O_3$ |
| | Rapamycin | RAPA, Rapemune, Siroimus, RPM, AY-22999 | $C_{31}H_{28}NO_{12}$ |
| | TGX-221 | | $C_{21}H_{24}N_4O_2$ |
| Histone Deacetylase & DNA-PK Inhibitors | NU-7441 | KU57788 | $C_{25}H_{19}NO_3S$ |
| | Trichostatin A | TSA | $C_{17}H_{22}N_2O_3$ |
| STAT Inhibitors | S31-201 | NSC 74859 | $C_{18}H_{15}NO_7S$ |
| Antimetabolites | Gemcitabine | Gemzar ® | $C_3H_{11}F_2N_8O_4HCl$ |
| Surviving inhibitor | LY2181308 | | |
| | Terameprecol | | |
| | YM155 | | |

Any of the disclosed compounds may be converted to a pharmaceutically acceptable salt. The pharmaceutically acceptable salt is not particularly limited as long as it is non-toxic. Non-limiting examples of salts with an inorganic or organic base include alkali metal salts (e.g. sodium salt, potassium salt and the like), alkaline earth metal salts (e.g. calcium salt, magnesium salt and the like), ammonium salts, amine salts (e.g. triethylamine salt), and the like. Non-limiting examples of acid addition salts derived from mineral acid (e.g. hydrochloride acid, hydrobromic acid, hydroiodic acid, phosphoric acid, nitric acid, sulphuric acid and the like), and salts derived from organic acids (e.g. tartaric acid, acetic acid, citric acid, malic acid, lactic acid, fumaric acid, maleic acid, benzoic acid, glycol acid, gluconic acid, succinic acid and the like).

Any of the disclosed compounds may be used as a prodrug for the below-mentioned pharmaceutical composition. As used herein, the term "prodrug" refers to any compound that can be converted to an active drug in vivo after administration, e.g. by being metabolized.

Administration of CIP2A dsRNAs and compounds of formula (I) may be concomitant, simultaneous, or subsequent.

Delivery of CIP2A specific dsRNAs can be accomplished in two principally different ways: 1) endogenous transcription of a nucleic acid sequence encoding the oligonucleotide, where the nucleic acid sequence is located in an expression construct or 2) exogenous delivery of the oligonucleotide.

For endogenous transcription, CIP2A specific dsRNAs may be inserted into suitable expression systems using methods known in the art. Non-limiting examples of such expression systems include retroviral vectors, adenoviral vectors, lentiviral vectors, other viral vectors, expression cassettes, and plasmids, such as those encapsulated in pegylated immunoliposomes (PILs), with or without one or more inducible promoters known in the art. Both dsRNA strands may be expressed in a single expression construct from the same or separate promoters, or the strands may be expressed in separate expression constructs.

The above-mentioned expression systems may also be used for the delivery of CIP2A silencing artificial miRNA precursors and shRNAs.

Typically, expression constructs are formulated into pharmaceutical compositions prior to administration to a human or animal subject (e.g. a canine subject). Administration may be performed by any suitable method known in the art, including systemic and local delivery. The formulation depends on the intended route of administration as known to a person skilled in the art. By way of example, the expression construct may be delivered in a pharmaceutically acceptable carrier or diluent, or it may be embedded in a suitable slow release composition. In some cases, the pharmaceutical composition may contain one or more cells producing the expression construct. Also bacteria may be used for RNAi delivery. For instance, recombinantly engineered *Escherichia coli* can enter mammalian cells after in vivo delivery and transfer shRNAs. A related approach is to use minicells derived e.g. from *Salmonella enterica*.

For exogenous delivery, dsRNA molecules are typically complexed with liposome or lipid-based carriers, cholesterol conjugates, or polyethyleneimine (PEI). A promising new approach is to complex dsRNAs with stable nucleic acid lipid particles (SNALPs). Suitable routes of administration for exogenous delivery, with or without said complexing, include, but are not limited to, parenteral delivery (e.g. intravenous injection), enteral delivery (e.g. orally), local administration, topical administration (.e.g. dermally or transdermally) as known to a person skilled in the art. Since surgical removal of a tumour is usually the primary clinical intervention, dsRNAs may be administered directly to the resected tumour cavity.

Chemotherapeutic agents of formula (I) may be administered to a human or animal subject by any suitable route known in the art including, but not limited to, those listed for the administration of CIP2A specific dsRNAs.

In the present combination therapy, dsRNA molecules and compounds of formula (I) may be formulated into the same or separate pharmaceutical composition. When separate pharmaceutical compositions are used, administration may be concomitant, simultaneous, or subsequent. The formulation and/or route of administration for dsRNA molecules and compounds of formula (I) may be selected independently from each other. In some embodiments, the pharmaceutical composition may comprise one or more different CIP2A silencing dsRNAs and/or one or more chemotherapeutic agents of formula (I).

The pharmaceutical compositions may be administered in any appropriate pharmacological carrier suitable for administration. They can be administered in any form that effect prophylactic, palliative, preventive or curing hyperproliferative diseases, such as cancer, in human or animal patients.

For the purposes of parenteral or topical administration, dsRNAs and/or compounds of formula (I) may be formulated, for instance, as solutions, suspensions or emulsions. The formulations may comprise aqueous or non-aqueous solvents, co-solvents, solubilizers, dispersing or wetting agents, suspending agents and/or viscosity agents, as needed. Non-limiting examples of non-aqueous solvents are propylene glycol, polyethylene glycol, vegetable oil, fish oil, and injectable organic esters. Aqueous carriers include, for instance, water, water-alcohol solutions, including saline and buffered medial parenteral vehicles including sodium chloride solution, Ringer's dextrose solution, dextrose plus sodium chloride solution, Ringer's solution containing lactose, or fixed oils. Non-limiting examples of intravenous vehicles include fluid and nutrient replenishers, electrolyte replenishers, such as those based on Ringer's dextrose and the like. Aqueous compositions may comprise suitable buffer agents, such as sodium and potassium phosphates, citrate, acetate, carbonate or glycine buffers depending on the targeted pH-range. The use of sodium chloride as a tonicity adjuster is also useful. The compositions may also include other excipients, such as stabilizing agents or preservatives. Useful stabilizing excipients include surfactants (polysorbate 20 & 80, poloxamer 407), polymers (polyethylene glycols, povidones), carbohydrates (sucrose, mannitol, glucose, lactose), alcohols (sorbitol, glycerol propylene glycol, ethylene glycol), suitable proteins (albumin), suitable amino acids (glycine, glutamic acid), fatty acids (ethanolamine), antioxidants (ascorbic acid, cysteine etc.), chelating agents (EDTA salts, histidine, aspartic acid) or metal ions (Ca, Ni, Mg, Mn). Among useful preservative agents are benzyl alcohol, chlorbutanol, benzalkonium chloride and possibly parabens.

Solid dosage forms for oral administration include, but are not limited to, capsules, tablets, pills, troches, lozenges, powders and granules. In such solid dosage forms, dsRNAs and/or compounds of formula (I) may be admixed with at least one inert diluent such as sucrose, lactose or starch. Such dosage forms may also comprise, as is normal practice, pharmaceutical adjuvant substances, e.g. stearate lubricating agents or flavouring agents. Solid oral preparations can also be prepared with enteric or other coatings which modulate release of the active ingredients.

Non-limiting examples of liquid dosage forms for oral administration include pharmaceutically acceptable emulsions, solutions, suspensions, syrups and elixirs containing inert non-toxic diluents commonly used in the art, such as water and alcohol. Such compositions may also comprise adjuvants, such as wetting agents, buffers, emulsifying, suspending, sweetening and flavouring agents.

The pharmaceutical composition may be provided in a concentrated form or in a form of a powder to be reconstituted on demand. In case of lyophilizing, certain cryoprotectants are preferred, including polymers (povidones, polyethylene glycol, dextran), sugars (sucrose, glucose, lactose), amino acids (glycine, arginine, glutamic acid) and albumin. If solution for reconstitution is added to the packaging, it may consist e.g., of sterile water for injection or sodium chloride solution or dextrose or glucose solutions.

Means and methods for formulating the present pharmaceutical preparations are known to persons skilled in the art, and may be manufactured in a manner which is in itself known, for example, by means of conventional mixing, granulating, dissolving, lyophilizing or similar processes.

The present combination therapy may be used to treat human or animal hyperproliferative diseases including, but not limited to psoriasis, myocardial hypertrophy, benign tumors such as adenoma, hamartoma and chondroma, as well as cancers such as squamous cell carcinomas of the head and neck, colon cancer, gastric cancer, breast cancer, ovarian cancer, prostate cancer, cervical cancer, esophageal cancer, lung cancer, liver cancer, brain cancers (e.g. gliomas, astrocytomas, and glioblastomas), and haematological cancers (e.g. chronic and acute T-cell and B-cell leukemias and lymphomas.).

As used herein, the term "treatment" or "treating" refers not only to complete cure of a disease, but also to prevention, alleviation, and amelioration of a disease or symptoms related thereto.

By an "efficient amount" of a combination of dsRNAs and compounds of formula (I) is meant an amount in which the harmful effects of a tumor are, at a minimum, ameliorated. Amounts and regimens for the administration of the present combination therapy can be determined readily by those with ordinary skill in the clinical art of treating cancer-related disorders. Generally, the dosage of the present combination therapy depend on considerations such as: age, gender and general health of the patient to be treated; kind of concurrent treatment, if any; frequency of treatment and nature of the effect desired; extent of tissue damage; duration of the symptoms; and other variables to be adjusted by the individual physician. A desired dose can be administered in one or more applications to obtain the desired results. Pharmaceutical compositions according to the present embodiments may be provided in unit dosage forms.

In one embodiment, dsRNAs may be administered in an effective amount within the dosage range of about 0.01 µg/kg to about 10 mg/kg, or about 1.0 µg/kg to about 10 µg/kg. DsRNAs may be administered in a single daily dose, or the total daily dosage may be administered in divided doses, e.g. of two, three or four times daily. In one embodiment, compounds of formula (I) may be administered in an effective amount within the dosage range of about 0.1 µg/kg to about 300 mg/kg, or about 1.0 µg/kg to about 10 mg/kg. The compounds of formula (I) may be administered in a single daily dose, or the total daily dosage may be administered in divided doses, e.g. of two, three or four times daily. The dosing schedule may be selected independently from the dosing schedule of dsRNAs.

It will be obvious to a person skilled in the art that, as the technology advances, the inventive concept can be implemented in various ways. The invention and its embodiments are not limited to the examples described below but may vary within the scope of the claims.

Example 1

CIP2A Inhibition Sensitizes T98G Cells to Various Chemotherapy Drugs

The human derived glioma cancer cells, T98G which express mutant p53, were transfected with either SCR siRNA (25 nM) or CIP2A siRNA (Seq ID #2; 25 nM). Following 48 h, media containing siRNA was replaced with media containing a chemotherapy drug at concentrations shown in FIG. 1. In order to determine if combining CIP2A inhibition with standard chemotherapy drugs would induce more potently apoptosis when compared to cells treated with either SCR siRNA or chemotherapy drugs alone, Caspase 3/7 activity (Caspase 3/7 glo assay, Promega) which is used to determine apoptosis induction in cells, was measured 48 h later according to the manufacturer's instructions. The results shown in FIG. 1, demonstrate that CIP2A siRNA alone does not induce apoptosis. However, combining CIP2A siRNA with either Lapatinib, Sunitinib; H-7; Vandetanib; Cisplatin; Paclitaxol; Temozolomide; Tandutinib or Indo)-3-carbinol, clearly enhanced the induction of apoptosis in T98G cells when compared to cells treated with CIP2A siRNA alone.

Example 2

CIP2A Inhibition Sensitizes HeLa Cells to Various Chemotherapy Drugs

Figure 2:
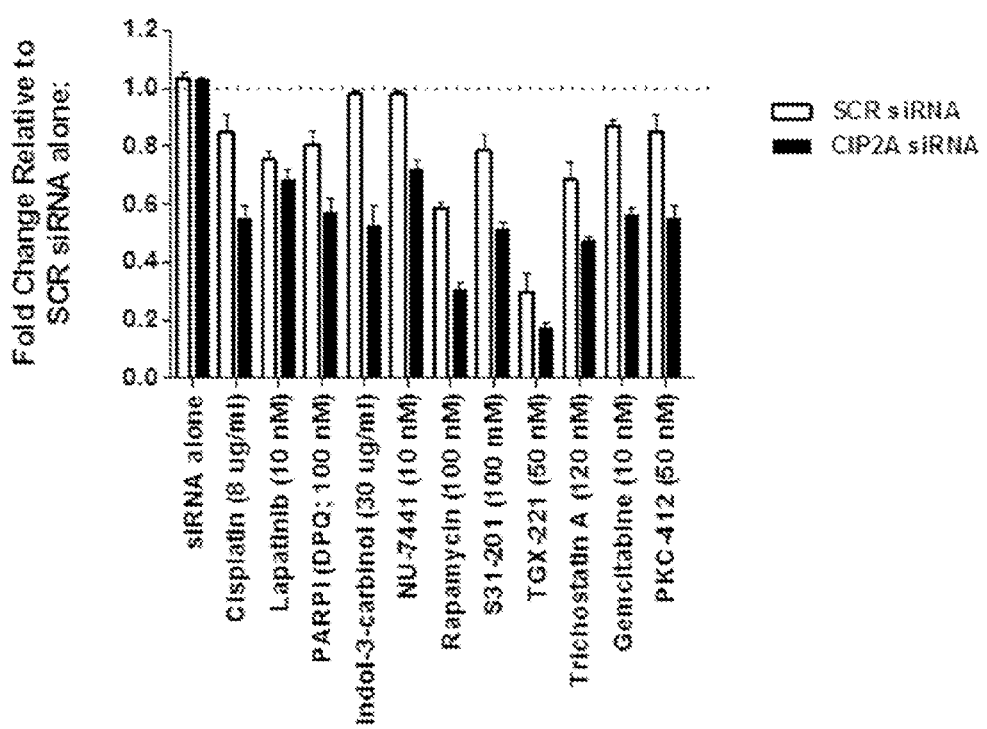
FIG. 2 shows the efficacy of CIP2A siRNA used in combination with various chemotherapy drugs to reduce cell viability as determined using the CTG assay, in the human derived cervical cancer cell line, HeLa, when compared to SCR siRNA alone.

The human derived cervical cancer cells, HeLa in which wt p53 fuction is blunted by HPV18 E6, were transfected with either SCR siRNA (25 nM) or CIP2A siRNA (Seq ID #6; 25 nM). Following 72 h, media containing siRNA was replaced with media containing a chemotherapy drug at concentrations shown in FIG. 2. In order to determine if combining CIP2A inhibition with standard chemotherapy drugs would reduce cell viability more potently when compared to cells treated with either SCR siRNA or chemotherapy drugs alone, the CTG assay (Promega) was used 48 h later, in accordance with the manufacturer's instructions. The results shown in FIG. 2, demonstrate that CIP2A siRNA alone has no effect on reducing cell viability. However, combining CIP2A siRNA with either Laptainib, PARPi (DPQ); Indo)-3-carbinol; NU-7441; Rapamycin; S31-201; TGX-221; Trichostatin A; Gemcitabine; or PKC-412 more potently reduced cell viabiltiy when compared to cells treated with CIP2A siRNA alone, indicating that inhibition of CIP2A sensitized HeLa cells to these chemotherapeutic drugs.

Example 3

Figure 3:
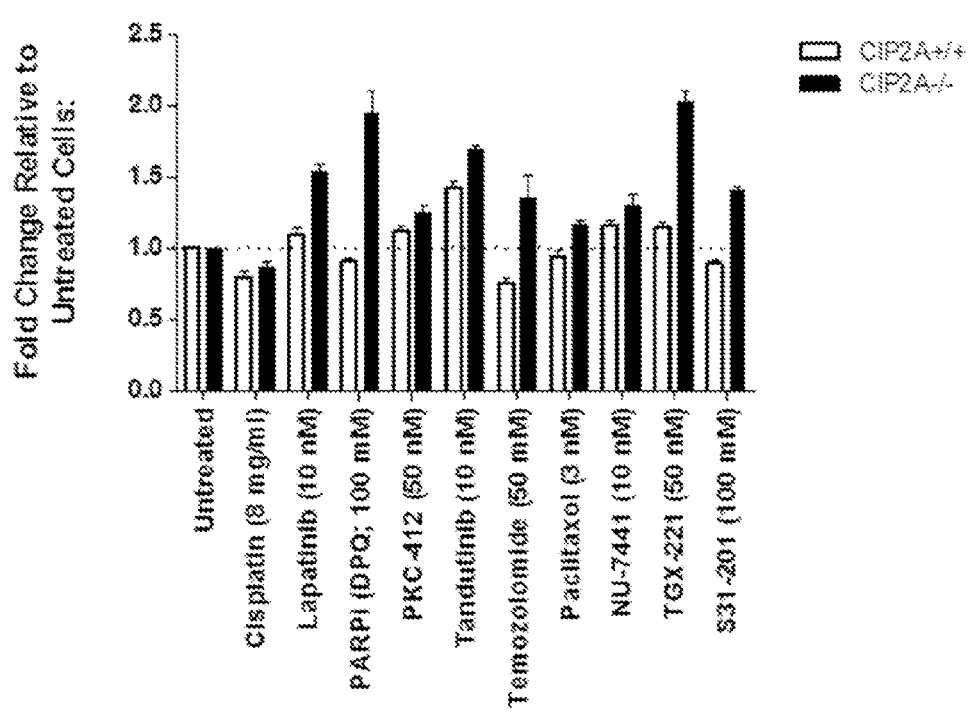
FIG. 3 demonstrates the efficacy of various chemotherapeutic drugs to induce apoptosis in primary mouse lymphoma cells derived from CIP2A deficient (CIP2A$^{-/-}$) mice or CIP2A expressing mice (CIP2A$^{+/+}$) mice, as determined using the Caspase 3/7 assay.

Primary Lymphoma Tumor Cells Derived from CIP2A Deficient (CIP2A$^{-/-}$) Mice are Sensitized to Chemotherapy Drugs Primary mouse Lymphoma tumor cell lines which express mutant p53, were derived from the spleen of CIP2A wild type (CIP2A$^{+/+}$) or CIP2A deficient (CIP2A$^{-/-}$) mice crossed with the Emu-myc mouse strain. Cells were seeded in 96-well plates and allowed to settle for 24 hours before 'normal growth' media was replaced with media containing chemotherapy drug at concentrations shown in FIG. 3. In order to determine if CIP2A deficient cancer cells were sensitized to chemotherapy drugs when compared with CIP2A expressing cancer cells, Caspase 3/7 activity (Caspase 3/7 glo assay, Promega) which is used to determine apoptosis induction in cells was measured 48 h later according to the manufacturer's instructions. The results shown in FIG. 3, demonstrate that apoptosis is more potently induced in lymphoma cells expressing extremely low CIP2A levels (CIP2A-/-) when treated with various chemotherapy drugs including: Lapatinib; PARPi (DPQ); PKC-412; Tandutinib; Temozolomide; Paclitaxol; NU-7441; TGX-221 or S31-201 in comparison to CIP2A expressing cells.

Example 4

Figure 4:
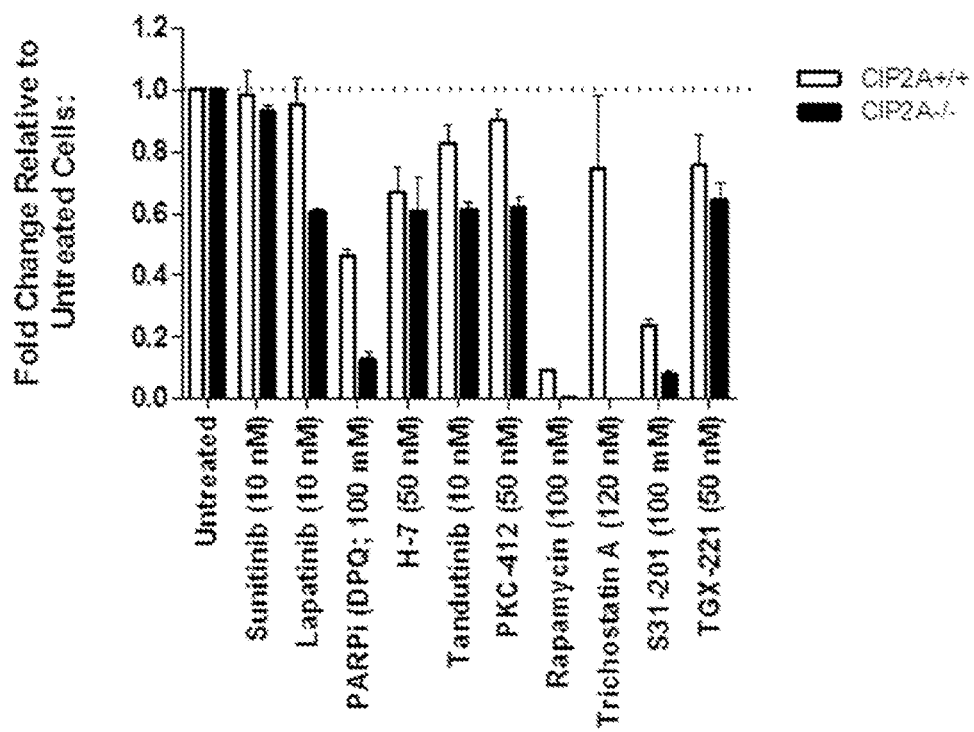
FIG. 4 demonstrates that cell viability, determined using the CTG assay, is significantly reduced in primary lymphoma cells derived from CIP2A deficient (CIP2A$^{-/-}$) mice when compared to cells expressing CIP2A, following the treatment of cells with various chemotherapy drugs.

Primary Lymphoma Tumor Cells Derived from CIP2A Deficient (CIP2A-/-) Mice are Sensitized to Chemotherapy Drugs, Resulting in Reduced Cell Viability Primary mouse Lymphoma tumor cell lines which express mutant p53, were derived from the spleen of CIP2A wild type (CIP2A$^{+/+}$) or CIP2A deficient (CIP2A$^{-/-}$) mice crossed with the Emu-myc mouse strain. Cells were seeded in 96-well plates and allowed to settle for 24 hours before 'normal growth' media was replaced with media containing chemotherapy drug at concentrations as shown in FIG. 4. In order to determine if treating CIP2A deficient cells with chemotherapy drugs would reduce cell viability when compared with CIP2A expressing cells, the CTG assay (Promega) was undertaken 48 h later according to the manufacturer's instructions. The results shown in FIG. 4, demonstrate that cell viability is more potently reduced in lymphoma cells expressing extremely low CIP2A levels (CIP2A-/-) treated with various chemotherapy drugs including: Lapatinib; PARPi (DPQ); H-7; Tandutinib; PKC-312; Rapamycin; Trichostatin A; S31-201 or TGX-221 when compared to cells expressing CIP2A.

Example 5

CIP2A Inhibition Sensitizes MKN28 Cells to Various Chemotherapeutic Drugs

Figure 5:
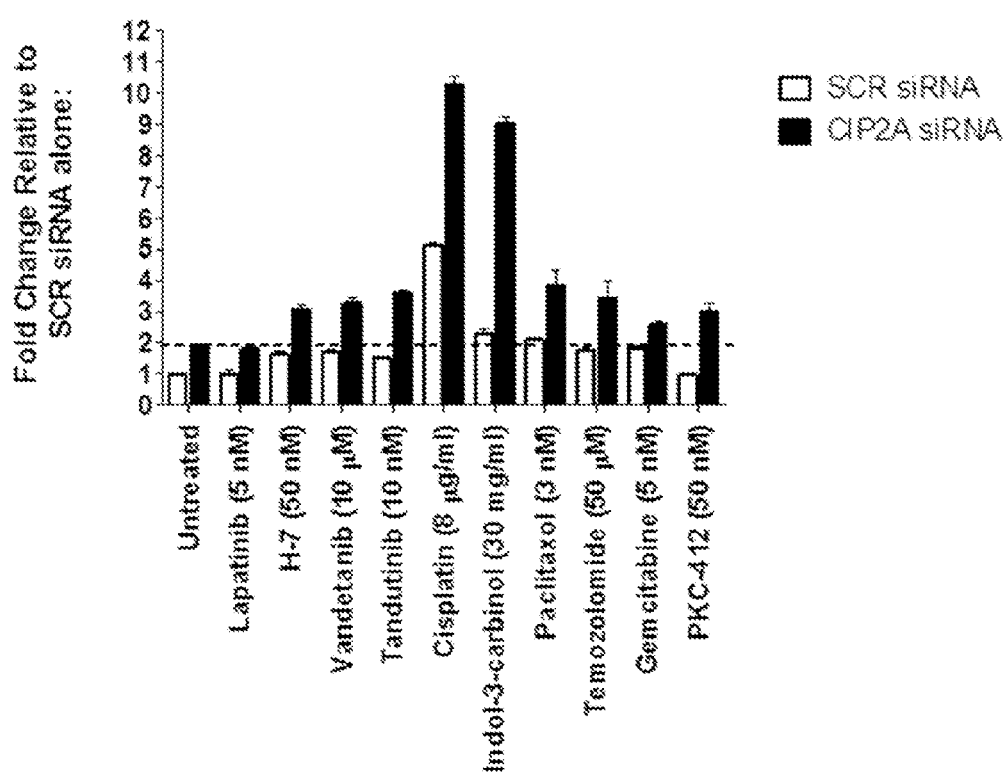
FIG. 5 is a Caspase 3/7 assay which measures the level of apoptosis (i.e. Caspase 3/7 activity) induced in the human derived gastric cancer cell line, MKN28, following the inhibition of CIP2A with siRNA in combination with standard chemotherapeutic agents when compared to SCR siRNA transfected cells alone.

The human derived gastric cancer cells, MKN28, which express mutant p53 were transfected with either SCR siRNA (25 nM) or CIP2A siRNA (Seq ID #6; 25 nM). Following 48 h, media containing siRNA was replaced with media containing a chemotherapy drug at concentrations shown in FIG. 5. In order to determine if combining CIP2A inhibition with standard chemotherapy drugs would induce apoptosis more potently when compared to cells treated with either SCR siRNA or chemotherapy drugs alone, Caspase 3/7 activity (Caspase 3/7 glo assay, Promega) which is used to determine apoptosis induction in cells, was measured 48 h later according to the manufacturer's instructions. The results shown in FIG. 5, demonstrate that CIP2A siRNA alone induced apoptosis when compared to MKN28 cells treated with SCR siRNA alone. However, the level of apoptosis is clearly enhanced when combining CIP2A siRNA with various chemotherapy drugs including: H-7, Vandetanib, Cisplatin, Paclitaxol, Temozolomide, Gemcitabine, PKC-412, Indol-3-carbinol and Tandutinib.

Example 6

Figure 6:
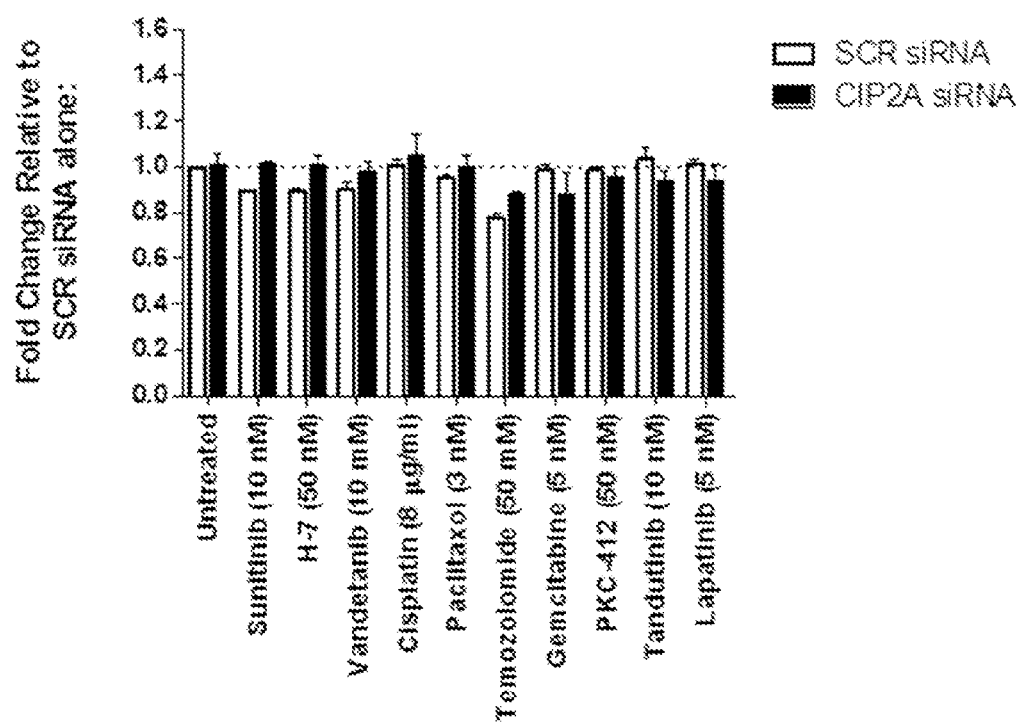
FIG. 6 demonstrates that apoptosis (i.e. Caspase 3/7 activity) is not induced in the human derived breast cancer cell line, MCF-7, following the inhibition of CIP2A with siRNA in combination with standard chemotherapeutic agents when compared to SCR siRNA transfected cells alone.

CIP2A Inhibition does not Sensitize MCF-7 Cells, which Express Wild Type p53, to Chemotherapeutic Drugs The human derived breast cancer cells, MCF-7, which express wild type p53 were transfected with either SCR siRNA (25 nM) or CIP2A siRNA (Seq ID #2; 25 nM). Following 48 h, media containing siRNA was replaced with media containing a chemotherapy drug at concentrations shown in FIG. 6. In order to determine if combining CIP2A inhibition with standard chemotherapy drugs would induce apoptosis significantly when compared to cells treated with either SCR siRNA or chemotherapy drugs alone, Caspase 3/7 activity (Caspase 3/7 glo assay, Promega) which is used to determine apoptosis induction in cells, was measured 48 h later according to the manufacturer's instructions. The results shown in FIG. 6, demonstrate that CIP2A siRNA alone did not induce apoptosis when compared to MCF-7 cells treated with SCR siRNA alone. Similarly, combining CIP2A siRNA with various chemotherapeutic drugs did not induce apoptosis in these cells expressing wild-type p53.

REFERENCES

Chari, N. S., N. L. Pinaire, L. Thorpe, L. J. Medeiros, M. J. Routbort, and T. J. McDonnell. 2009. The p53 tumor suppressor network in cancer and the therapeutic modulation of cell death. *Apoptosis.* 14:336-47.

Cui, W., J. Ning, U. P. Naik, and M. K. Duncan. 2004. OptiRNAi, an RNAi design tool. *Comput Methods Programs Biomed.* 75:67-73.

Junttila, M. R., P. Puustinen, M. Niemela, R. Ahola, H. Arnold, T. Bottzauw, R. Ala-Aho, C. Nielsen, J. Ivaska, Y. Taya, S. L. Lu, S. Lin, E. K. Chan, X. J. Wang, R. Grenman, J. Kast, T. Kallunki, R. Sears, V. M. Kähäri, and J. Westermarck. 2007. CIP2A Inhibits PP2A in Human Malignancies. *Cell.* 130:51-62.

Khanna, A., C. Bockelman, A. Hemmes, M. R. Junttila, J. P. Wiksten, M. Lundin, S. Junnila, D. J. Murphy, G. I. Evan, C. Haglund, J. Westermarck, and A. Ristimaki. 2009. MYC-dependent regulation and prognostic role of CIP2A in gastric cancer. *J Natl Cancer Inst.* 101:793-805.

Kim, D. H., M. A. Behlke, S. D. Rose, M. S. Chang, S. Choi, and J. J. Rossi. 2005. Synthetic dsRNA Dicer substrates enhance RNAi potency and efficacy. *Nat. Biotechnol.* 23:222-6.

Li, Q. X., P. Tan, N. Ke, and F. Wong-Staal. 2007. Ribozyme technology for cancer gene target identification and validation. *Adv Cancer Res.* 96:103-43.

Silva, J. M., M. Z. Li, K. Chang, W. Ge, M. G. Golding, R. J. Rickles, D. Siolas, G. Hu, P. J. Paddison, M. R. Schlabach, N. Sheth, J. Bradshaw, J. Burchard, A. Kulkarni, G. Cavet, R. Sachidanandam, W. R. McCombie, M. A. Cleary, S. J. Elledge, and G. J. Hannon. 2005. Second-generation shRNA libraries covering the mouse and human genomes. *Nat. Genet.* 37:1281-8.

Vassilev, L. T., B. T. Vu, B. Graves, D. Carvajal, F. Podlaski, Z. Filipovic, N. Kong, U. Kammlott, C. Lukacs, C. Klein, N. Fotouhi, and E. A. Liu. 2004. In vivo activation of the p53 pathway by small-molecule antagonists of MDM2. *Science.* 303:844-8.

Westermarck, J., and W. C. Hahn. 2008. Multiple pathways regulated by the tumor suppressor PP2A in transformation. *Trends Mol. Med.* 14:152-60.

Zhao, J. J., T. M. Roberts, and W. C. Hahn. 2004. Functional genetics and experimental models of human cancer. *Trends Mol. Med.* 10:344-50.

The invention claimed is:

1. A composition comprising a combination of:
at least one type of a CIP2A silencing agent selected from the group consisting of an siRNA molecule having at least 80% sequence identity to a sequence selected from SEQ ID NOS: 1-5 and having CIP2A silencing activity, and an shRNA molecule having at least 80% sequence identity to a sequence selected from SEQ ID NOS: 10-13 and 19 and having CIP2A silencing activity;
at least one compound selected from the group consisting of PKC-412, PARP inhibitor III, indol-3-carbinol, cisplatin, rapamycin, TGX-221, NU-7441, S31-201, and gemcitabine; and
at least one pharmaceutically acceptable carrier.

2. The composition according to claim 1, suitable for use in the treatment of a hyperproliferative disease selected from a group consisting of psoriasis, myocardial hypertrophy, benign tumors, solid cancers and haematological cancers.

3. The composition according to claim 2, wherein said solid cancer is selected from a group consisting of squamous cell carcinomas of the head and neck, colon cancer, gastric cancer, breast cancer, ovarian cancer, prostate cancer, cervical cancer, esophageal cancer, lung cancer, liver cancer, brain cancer, glioma, astrocytoma, and glioblastoma and haematological cancers is selected from a group consisting of acute and chronic T-cell and B-cell leukemias and lymphomas.

* * * * *